United States Patent
Ross et al.

(10) Patent No.: US 10,860,621 B1
(45) Date of Patent: Dec. 8, 2020

(54) SYSTEMS AND METHODS FOR DATABASE MANAGEMENT

(71) Applicant: Massachusetts Mutual Life Insurance Company, Springfield, MA (US)

(72) Inventors: Gareth Ross, Amherst, MA (US); Yaron Ben-Zvi, Hastings on Hudson, NY (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 557 days.

(21) Appl. No.: 15/135,007

(22) Filed: Apr. 21, 2016

Related U.S. Application Data

(60) Provisional application No. 62/150,372, filed on Apr. 21, 2015.

(51) Int. Cl.
| | |
|---|---|
| *G16H 50/70* | (2018.01) |
| *G06F 16/28* | (2019.01) |
| *G16H 40/63* | (2018.01) |
| *G16H 50/30* | (2018.01) |
| *G16H 10/60* | (2018.01) |

(52) U.S. Cl.
CPC .......... *G06F 16/287* (2019.01); *G06F 16/288* (2019.01); *G16H 10/60* (2018.01); *G16H 40/63* (2018.01); *G16H 50/30* (2018.01); *G16H 50/70* (2018.01)

(58) Field of Classification Search
CPC ......... G06F 17/30601; G06F 17/30707; G06F 17/30595; G06F 17/3061; G06F 17/30864; G06F 17/2735; G16H 10/60; G16H 50/30

See application file for complete search history.

(56) References Cited

U.S. PATENT DOCUMENTS

| | | | |
|---|---|---|---|
| 5,692,501 A | 12/1997 | Minturn | |
| 6,656,125 B2 | 12/2003 | Misczynski et al. | |
| 8,475,367 B1 | 7/2013 | Yuen et al. | |
| 8,615,487 B2 | 12/2013 | Gomez et al. | |
| 8,776,168 B1 | 7/2014 | Gibson et al. | |
| 9,086,292 B2 * | 7/2015 | Horvitz | G01C 21/3697 |
| 9,690,937 B1 | 6/2017 | Dunchin et al. | |
| 2007/0100595 A1 | 5/2007 | Earles et al. | |
| 2008/0162496 A1 | 7/2008 | Postrel | |
| 2011/0046519 A1 | 2/2011 | Raheman | |
| 2013/0027428 A1 | 1/2013 | Graham et al. | |
| 2013/0030260 A1 | 1/2013 | Hale | |
| 2014/0163927 A1 * | 6/2014 | Molettiere | A61B 5/0002 |
| | | | 702/189 |
| 2014/0164519 A1 * | 6/2014 | Shah | H04L 67/306 |
| | | | 709/204 |
| 2014/0278220 A1 * | 9/2014 | Yuen | G01B 21/16 |
| | | | 702/150 |

(Continued)

*Primary Examiner* — Ashish Thomas
*Assistant Examiner* — Suman Rajaputra
(74) *Attorney, Agent, or Firm* — Foley & Lardner LLP

(57) ABSTRACT

Embodiments in the present disclosure may be directed to provide systems and methods for operating database and performing record set specific computing operations. The disclosed method may operate one or more client computing devices, an analytical engine, one or more wearable devices operatively coupled to one or more client computing devices via a communication network, and one or more databases. The disclosed method may include steps performed by a processor for tracking users to create or join groups with similar lifestyles attributes.

7 Claims, 8 Drawing Sheets

(56) References Cited

U.S. PATENT DOCUMENTS

| | | | |
|---|---|---|---|
| 2014/0278614 A1* | 9/2014 | Delost | G06Q 10/025 705/6 |
| 2014/0350970 A1* | 11/2014 | Schumann, Jr. | G08G 1/096775 705/4 |
| 2015/0006274 A1* | 1/2015 | Calbucci | G06Q 30/0226 705/14.27 |
| 2016/0086285 A1* | 3/2016 | Jordan Peters | G06Q 40/08 705/4 |
| 2017/0221149 A1* | 8/2017 | Hsu-Hoffman | G06Q 40/08 |

* cited by examiner

SYSTEMS AND METHODS FOR DATABASE MANAGEMENT

CROSS-REFERENCE TO RELATED APPLICATIONS

This application claims a benefit of priority to U.S. Provisional Patent Application Ser. No. 62/150,372, filed on Apr. 21, 2015, which is herein fully incorporated by reference in its entirety.

TECHNICAL FIELD

Generally, the present disclosure relates databases. More particularly, the present disclosure relates to file management and data structures.

BACKGROUND

A database stores a set of records. However, managing such records may be difficult due to record number, size, content, or relationships. For example, there may be a need to organize records into different sets and use such sets to perform various set-specific computing operations. Thus, a need exists for a technology to organize database records into different sets in order to execute set-specific computing operations.

SUMMARY

One embodiment comprises a method of managing databases, the method comprising: accessing, by an application server, over a wide area network, a plurality of records stored in a first database, wherein the first database is managed by a first database management system, wherein the first database and the first database management system are hosted on a first database server, wherein each of the records comprises a social network service profile, wherein each of the social network service profiles comprises a profile identifier, an electronic messaging address, and a health lifestyle identifier; identifying, by the application server, the health lifestyle identifiers in the records; reading, by the application server, the health lifestyle identifiers from the records; comparing, by the application server, the health lifestyle identifiers; in response to determining, by the application server, that the health lifestyle identifiers are related in content: creating, by the application server, a record in a second database, wherein the second database is managed by a second database management system, wherein the second database and the second database management system are hosted on a second database server, wherein the application server and the second database server are in a local area network, wherein the first database server is external to the local area network; configuring, by the application server, via the second database management system, the record in the second database to be searchable in the second database via the health lifestyle identifiers; copying, by the application server, from the first database, via the first database management system, the profile identifiers and the electronic messaging addresses; populating, by the application server, via the second database management system, the record with the profile identifiers and the electronic messaging addresses based on the copying; generating, by the application server, an electronic message; accessing, by the application server, the electronic messaging addresses in the record of the second database via the second database management system; sending, by the server, the electronic message to the electronic messaging addresses.

Numerous other aspects, features and benefits of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DEFINITIONS

Figure 1:
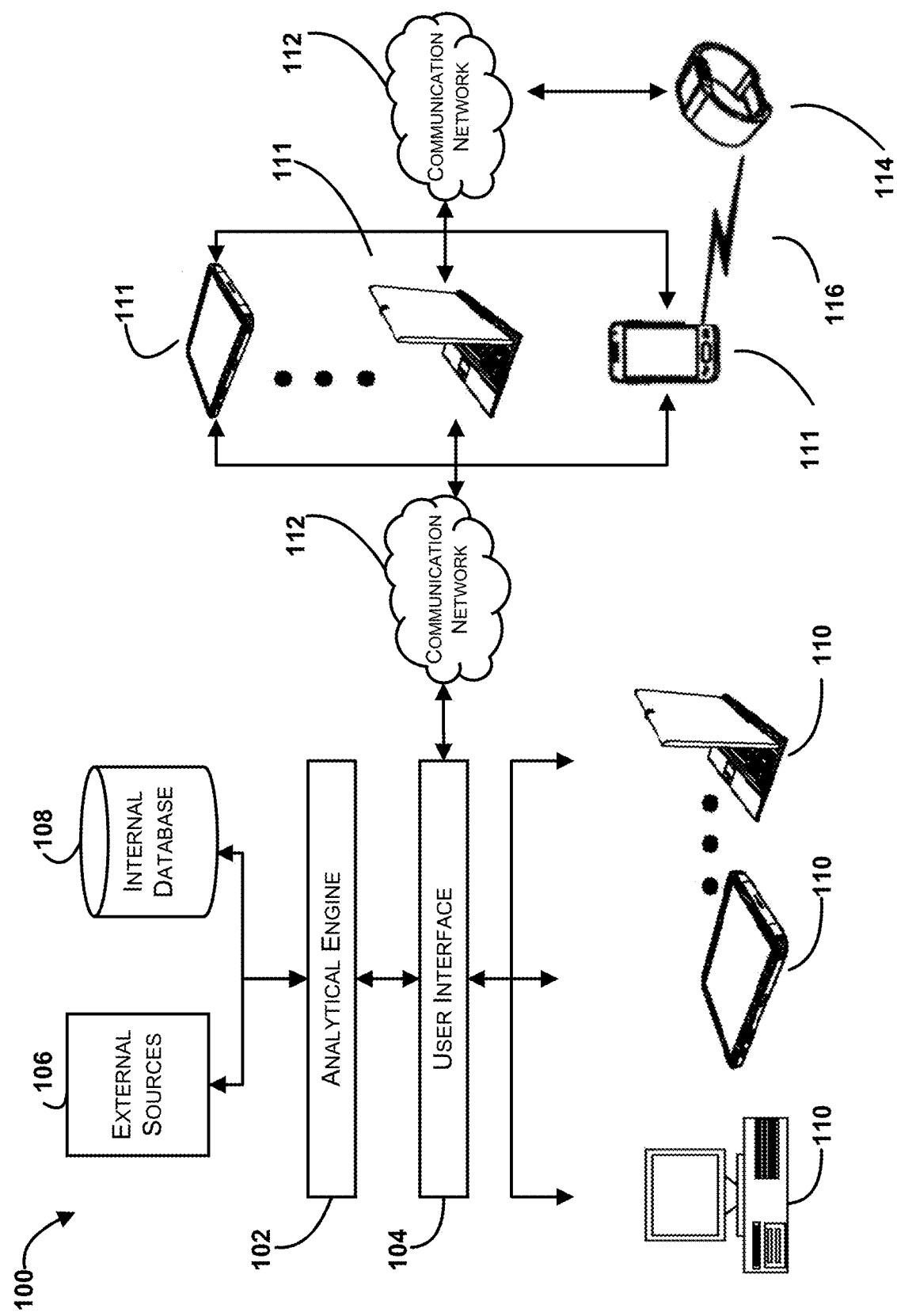
FIG. 1 is a block diagram illustrating a system for tracking users to create or join groups with similar lifestyles attributes, according to an embodiment.

As used here, the following terms may have the following definitions:

"Analytical engine" refers to a software module that handles data integration, breaks data streams into atomic parts, executes rules, and performs data matching by using fuzzy logic, among others.

DETAILED DESCRIPTION

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

In some embodiments, the impact of wearables is already being felt in education, communication, navigating, and entertainment. However, the greatest potential of wearable devices may lie in healthcare. Wearables are able to track activity, fitness, and lifestyle. Therefore, wearable devices may have the potential to disrupt the health in various ways.

Additionally, with the advent of social media, customers can now provide and have access to a variety of information about their friend's lives. The availability of such information can have a positive impact on a person's life if it can be channeled to areas of interest, such as diet, fitness, healthy lifestyle, and the like. Furthermore, the addition of information gathered from wearables can provide a great amount of motivation to people connected through social media websites. Under the right conditions, the information collected from wearable as well as the potential motivation from social media may enable targeted electronic messaging.

A system and method for issuing an electronic document based on collected biometric data are disclosed. According to an embodiment, an analytical engine operates in a system that includes a user interface, external data sources, an internal database, client computing devices, a communication network, wearables, and a communication link. It should be understood that the system can include less components, more components, or different components depending on desired analysis goals.

In an illustrative operation, an analytical engine receives data from external data sources. The analytical engine then processes data received from the external data sources and creates address leads that are stored in an internal database. The analytical engine runs an electronic messaging campaign using the leads previously stored in the internal database. The analytical engine generates a user interface in which a user interacts with system via client computing devices and a communication network. The analytical engine manages accounts created by group of users. The analytical engine receives biometric data from group of users using wearables. The analytical engine processes biometric data of group of users and produces statistics. The analytical engine suggests reward messages for group of users that show healthy lifestyles during a standard period of time.

According to some embodiments, an exemplary illustration of a user interface for a mobile application (Fitness/LifeStyle App) for monitoring the Fitness/LifeStyle of a group of users is disclosed. In these embodiments, the mobile application includes the following exemplary functions: allowing the user to create and manage a user account in the system; allowing the user to see the available workouts; allowing the user to invite and look at friends list; allowing the user to look at friends activity; allowing the user to look at workout history of the user and friends; allowing the user to check rewards for achieving goals; allowing the user to perform searches of people to send friend requests; allowing the user to see the user name of the person connected to the system; allowing the user to receive emails from the an operator of the system; and allowing the user to see connection status.

According to some embodiments, a method for issuing an electronic document to users that volunteered to form groups that use wearables so as to monitor their fitness and lifestyle and report back to an operator of the system is disclosed. In these embodiments, the method includes a plurality of steps performed by a processor. The steps may include: extracting data from external sources; processing and storing data in the internal database; running a an electronic messaging campaign to attract users to join a messaging group; managing groups of registered users; issuing an electronic document to registered users; and sending messages to the messaging groups based on their achievements, as obtained via the wearables.

According to some embodiments, a method for operating a mobile application used for monitoring fitness/lifestyle of one or more users. In these embodiments, the method includes a plurality of steps performed by a processor. The steps may include: downloading and installing Fitness/LifeStyle App on client computing devices; creating accounts for users that volunteer to join a group; inviting friends to create groups of users with similar lifestyles; setting up wearables; monitoring and collecting biometrics of groups of users; and sending biometrics of groups to the server.

One computer-implemented embodiment may include a method that extracts user data associated with users from an external source, the user data including information indicative of lifestyles of the respective users. The user data may be processed to populate a database, and the user data may be stored in the database. The user data stored in the database may be queried for users having attributes indicative of similar lifestyles. A social network user identifier of each user of the set of users having attributes indicative of similar lifestyles may be obtained. An electronic messaging content may be communicated to the social network user identifier of each user in the set of users having attributes indicative of similar lifestyles. A change in risk level for the set of users having attributes indicative of similar lifestyles may be calculated.

One embodiment of a method may include creating accounts for users who are associated with a biometric monitoring program. Users may be enabled to create groups of users associated with the biometric monitoring program, and having similar lifestyles using a downloadable application installed on a computing device of a user. Biometric data being monitored by a wearable device being used by respective users in a group of users having similar lifestyles may be collected. The biometric data collected by respective wearable devices of the users in the group may be processed to determine whether the group qualifies to receive a reward message. A listing of the users in the group and associated biometric data from the users in the group may be transmitted.

One computer-implemented method may include receiving geolocation data associated with users throughout a time period. A determination to identify at least a subset of users with similar risk profiles may be made based on the geolocation data. The user(s) with similar risk profiles may be enabled to form or join groups of users with similar risk profiles via a social network. A record of the group of users with similar risk profiles may be established. Risk for group of users based upon the similar risk profiles at the end of the time period may be calculated. The calculated risk may be utilized for issuing an electronic document, which may comprise a plurality of formatted paragraphs.

A computer-implemented process may include collecting biometric data of at least one biometric parameter and geolocation data over at least one time period from a wearable device. A risk factor score for a user may be generated based on biometric data of the at least one biometric parameter and geolocation data over the at least one time period to be used for issuing an electronic document to the users. An input of answers to a questionnaire form about the users may be received, and a risk level of the users based on the answers and risk factor score may be calculated, where the risk level may be calculated independent of paramed data.

System Components and Architecture

FIG. 1 is a block diagram illustrating a system for tracking, motivating, and groups of users to create or join social media groups that are concerned with lifestyle and fitness, and receive periodic reward messages based on the group's behavior.

According to one embodiment, system 100 includes analytical engine 102, user interface 104, external sources 106, internal database 108, client computing devices 110, communication network 112, wearables 114, and link 116. It should be understood that system 100 and analytical engine 102 can include less components, more components, or different components depending on desired analysis goals.

According to an embodiment, analytical engine 102 further includes one or more data extraction modules, one or more data processing modules, and one or more APIs. The modules and/or APIs contained/operating within analytical engine 102 are further described in FIG. 3. Each of the sub-components within analytical engine 102 may be a set of computer instructions executed by central processing units that run computer executable program instructions or related algorithms. Each central processing unit may be a component of computing devices such as a server, a single computer, or multiple computers in a distributed configuration. In an example, a central processing unit as described in FIG. 2 below can be implemented within the aforementioned computing devices.

In FIG. 1, analytical engine 102 is operatively coupled to and in bi-directional communication with user interface 104, external sources 106, internal database 108, and client computing devices 110. User interface 104 is further operatively coupled to and in bi-directional communication with client computing devices 111, and wearables 114, and wearables 114 are wirelessly coupled to and in bi-directional communication with computing devices 111 via link 116. Each of the different components of system 100 may be implemented in any type of suitable processor-controlled device that receives, processes, and/or transmits digital data, configured as further described below and in FIG. 2. Examples of devices incorporating one or more suitable processor-controlled devices include smartphones, desktop computers, laptop computers, servers, tablets, PDAs, specialized computing platforms biometric data processing, and the like. Examples of devices may include smartphones, desktop computers, laptop computers, tablets, and PDAs, among others. Examples of link 116 include any short-ranged wireless protocol, such as, for example Bluetooth, BTLE, Bluetooth Smart, Wi-Fi, Zigbee, and the like.

In FIG. 1, analytical engine 102 may be implemented as software that runs on a server including a processing unit for running related algorithms or computer executable program instructions. Processing unit may include a processor with computer-readable medium, such as a random access memory (RAM) coupled to the processor. Examples of processor may include a microprocessor, application specific integrated circuit (ASIC), and field programmable object array (FPOA), among others. In some embodiments, analytical engine 102 receives data from external sources 106, and internal database 108. In these embodiments, analytical engine 102 processes the received data and stores the processed data at internal database 108. In further embodiments, analytical engine 102 generates user interface 104 in which a user interacts with system 100 via client computing devices 110. Examples of data received from external sources 106 include address leads gathered from social networks of users that may exhibit a healthy lifestyle such as, for example, users that workout, users that jog/run every day, users that do yoga, and the like. Examples of data stored in internal database 108 include processed address leads that are included in a electronic messaging campaign.

The electronic messaging campaign offers users that have similar lifestyles a way to create or join groups that can then be monitored using wearables 114 with biometric sensors, and receive an incentive electronic message. The biometric sensors may be of a wide variety to sense heart rate (e.g., heart rate monitor), sweat, oxygen levels, motion, steps (e.g., pedometer or smartphone with appropriate app), or otherwise. A sensor, such as a Fitbit® or comparable device, may be utilized.

In one or more embodiments, external sources 106 and internal database 108 are implemented as relational databases that provide functions of fetching, indexing, and storing data. For example, the relational database can manage records based on primary keys. External sources 106 and internal database 108 may be implemented through database management systems (DBMS), such as, MySQL, PostgreSQL, SQLite, Microsoft SQL Server, Microsoft Access, Oracle, SAP, dBASE, FoxPro, IBM DB2, LibreOffice Base, FileMaker Pro, and/or any other type of database that may organize collections of data.

In one or more embodiments, user interface 104 can be implemented as software that is configured to communicate with a user and that runs on any type of computing device. In these embodiments, user interface 104 communicates with client computing devices 111 so as to allow users of system 100 to manage personal data. Examples of users of system 100 include authorized personnel, and users that created an account within system 100.

In further embodiments, user interface 104 receives an application from analytical engine 102 that is displayed on client computing devices 110. User interface 104 grants access to users to perform one or more document generation tasks within system 100. For example, the document can include formatted paragraphs. Examples of the tasks include determining risk scores of groups of users based on biometric data received from those groups. In still further embodiments, user interface 104 receives an application programming interface (API) from analytical engine 102 that is displayed on client computing devices 111. User interface 104 grants access to users to manage their user accounts within system 100. Examples of an application are further described in FIG. 4.

In one or more embodiments, wearables 114 are clothing and accessories incorporating computer and advanced electronic technologies. In these embodiments, wearables 114 read biometric data from one or more users, and send biometric data readings from one or more users to an application installed on client computing devices 111. Examples of biometric data include number of steps per day, heartbeat rates, levels of sweat, O2 saturation, and the like. Client computing devices 111 compute and send biometric data via communication network 112. Examples of wearables 114 include smartwatches, trackers, pedometers, activity trackers, and the like. In one embodiment, a client computing device (e.g., smartphone) with the ability to sense and generate biometric data (e.g., number of steps) may be utilized, as well, thereby reducing or eliminating the need for a wearable device.

In exemplary operation, analytical engine 102 receives data from external sources 106. Analytical engine 102 then processes data received from external sources 106 and creates leads that it stores in internal database 108. Analytical engine 102 runs an electronic messaging campaign using the address leads previously stored in internal database 108. Analytical engine 102 generates user interface 104 in which a user and/or users interact with system 100 via client computing devices 110 and 111 via communication network 112. Analytical engine 102 manages accounts created by groups of users. Analytical engine 102 receives biometric data from members of groups of users using wearables 114. Analytical engine 102 processes biometric data received from the group of users and produces statistics that can be used by a user to generate an electronic document comprising formatted paragraphs to groups of users reporting biometric data to the server. Analytical engine 102 suggests reward messages for group of users that show healthy lifestyles during a standard period of time. In suggesting reward messages, the analytical engine 102 may determine how much of one or more biometric parameters (e.g., number of steps, number of workouts per week, etc.) a group of users as a whole (e.g., collective average number of workouts per week by each of the group members) performs.

Figure 2:
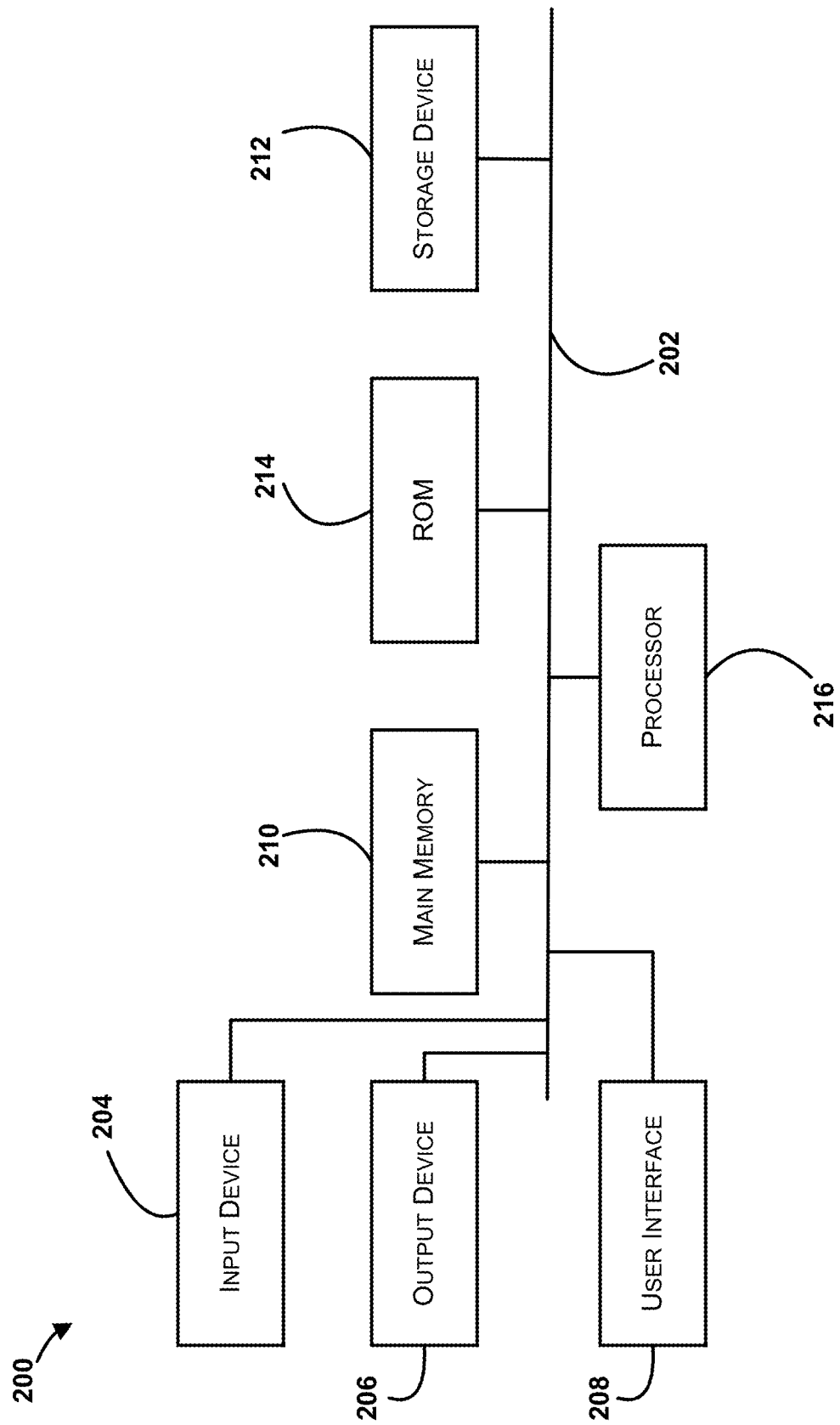
FIG. 2 is a block diagram of an exemplary computing device in which one or more embodiments of the present disclosure may operate, according to an embodiment.

FIG. 2 is a diagram of example components of computing device 200 or server, according to an exemplary embodiment. According to some aspects of this embodiment, computing device 200 includes bus 202, input device 204, output device 206, user interface 208, main memory 210, storage device 212, read only memory (ROM 214) and processor 216. In another exemplary embodiment, server includes additional, fewer, different, or differently arranged components than are illustrated in FIG. 2.

In one embodiment, bus 202 coordinates the interaction and communication among the components of the server. Input device 204 includes a mechanism that permits a user to input information to computing device 200, such as a keyboard, a mouse, a button, a pen, a touch screen, voice recognition and/or biometric mechanisms, etc. Output device 206 includes a mechanism that outputs information to the operator, including a display, a light emitting diode (LED), and a speaker, among others.

User interface 208 enables computer interactions with other devices and/or systems via a network connection. Network connections may refer to any suitable connection between computers such as intranets, local area networks (LAN), cloud networks, virtual private networks (VPN), wireless area networks (WAN), and the internet, among others.

Main memory 210 includes a random access memory (RAM) or another type of dynamic storage device that may store information and instructions for execution by processor 216. ROM 214 includes a ROM device or another type of static storage device that may store static information and instructions for use by processor 216. Processor 216 includes a microprocessor, an application specific integrated circuit (ASIC), and a field programmable object array (FPOA), among others, that may interpret and execute instructions.

According to some aspects of this embodiment, server, using one or more suitable software modules, enables data fetching, biometrics processing tasks, and predictive analytics. The server performs these operations in response to processor 216 executing software instructions contained in a computer-readable medium, such as main memory 210.

The software instructions reads into main memory 210 from another computer-readable medium, such as storage device 212, or from another device via user interface 208. The software instructions contained in main memory 210 may cause processor 216 to perform processes that will be described later. Alternatively, hardwired circuitry may be used in place of or in combination with software instructions to implement processes described herein. Thus, implementations described herein are not limited to any specific combination of hardware circuitry and software.

Figure 3:
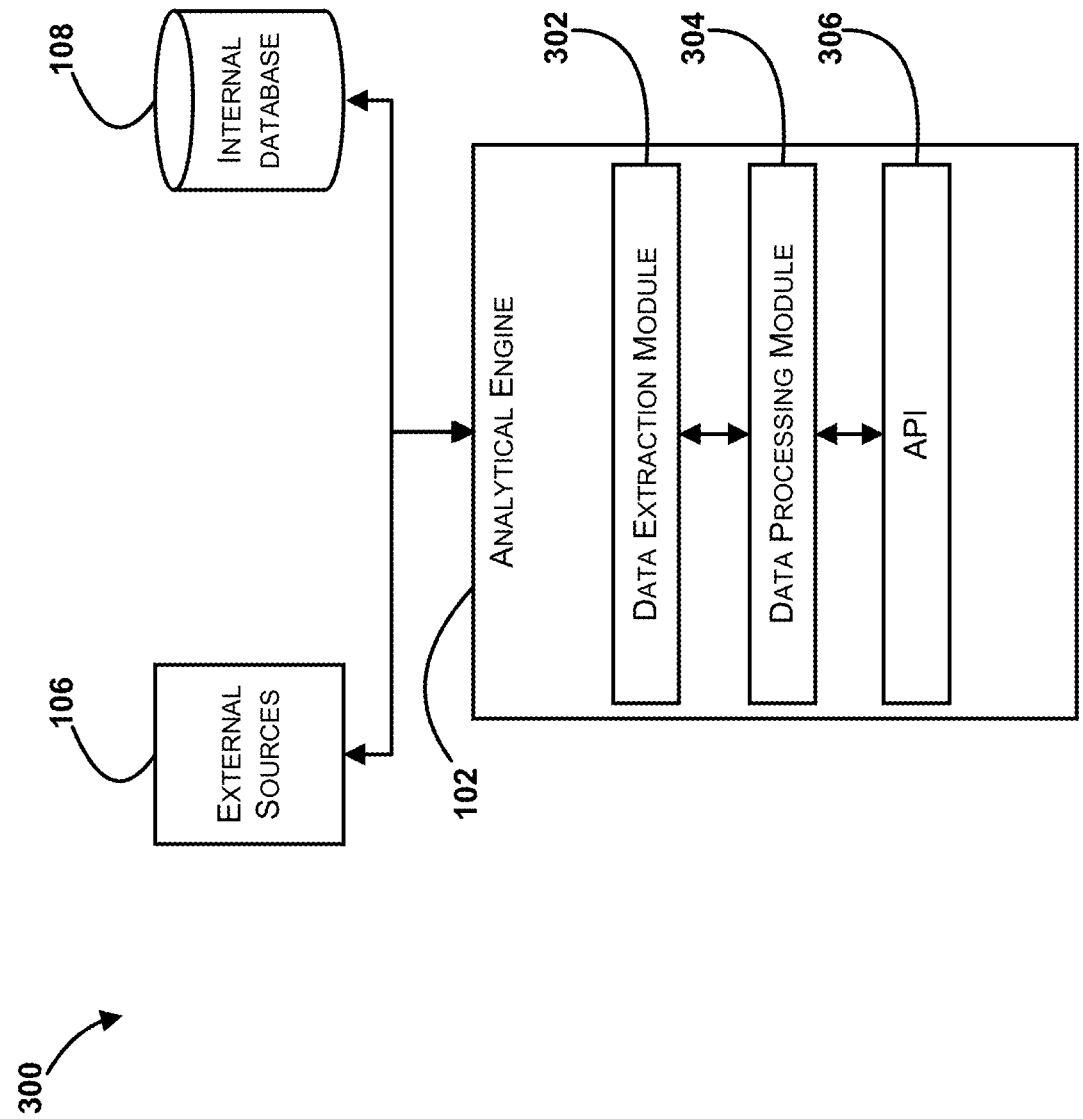
FIG. 3 is a block diagram illustrating a portion of the system pertaining to an analytical engine, according to an embodiment.

FIG. 3 is a block diagram illustrating a subsystem of the system pertaining to analytical engine 102 of FIG. 1. In FIG. 3, subsystem 300 includes external sources 106, internal database 108, analytical engine 102, data extraction module 302, data processing module 304, and API 306. It should be understood that subsystem 300 can include less components, more components, or different components depending on the desired analysis goals. In an example, external sources 106, internal database 108, analytical engine 102, data extraction module 302, data processing module 304, and API 306 are implemented as external sources, internal database, analytical engine, data extraction module, data processing module, and API described in system 100 of FIG. 1.

Analytical engine 102 is operatively coupled to and in bi-directional communication with data extraction module 302, data processing module 304, and API 306. Analytical engine 102 is further operatively coupled to and in bi-directional communication with external sources 106 and internal database 108.

In one or more embodiments, data extraction module 302 within analytical engine 102 is implemented as one or more computer software modules that include programmatic rules or executing/running different algorithms that allow data fetching and data indexing of potential address leads gathered from social networks. In these embodiments, data extraction module 302 is configured to fetch and index from social networks data associated with users showing similar lifestyles. This data is indicative of a lifestyle of a user, and can be used to identify potential leads for grouping together users into social networking groups for beneficial results. Examples of potential leads include users that may exhibit a healthy lifestyle such as, for example, users that workout, eat healthy, jog/run every day, do sports, and the like.

In one or more embodiments, data processing module 304 within analytical engine 102 is implemented as one or more computer software modules that include programmatic rules or executing/running different algorithms that allow data fetching, data indexing, and data storing of potential leads gathered from data extraction module 302. In these embodiments, data processing module 304 is configured to rank potential leads based on their lifestyle and produce a list of address leads that are stored within internal database 108 to later be included in future an electronic messaging campaigns. The an electronic messaging campaign offers users having similar lifestyles to create or join groups that can then be monitored using wearables with biometric sensors. These groups may then be eligible or qualify to receive incentive messages as a reward for healthy behavior. Examples of rewards include coupons for workout clothing, etc.

In one or more embodiments, API 306 within analytical engine 102 is any Representational State Transfer Application Programming Interface (REST API) that controls and manages one or more APIs. In these embodiments, API 306 provides web services to one or more mobile applications installed on the client computing devices. Examples of web services include showing data on a website, uploading large amounts of data that will later be consumed by a mobile app, downloading data to run custom analytics, exporting data, and the like.

Figure 4:
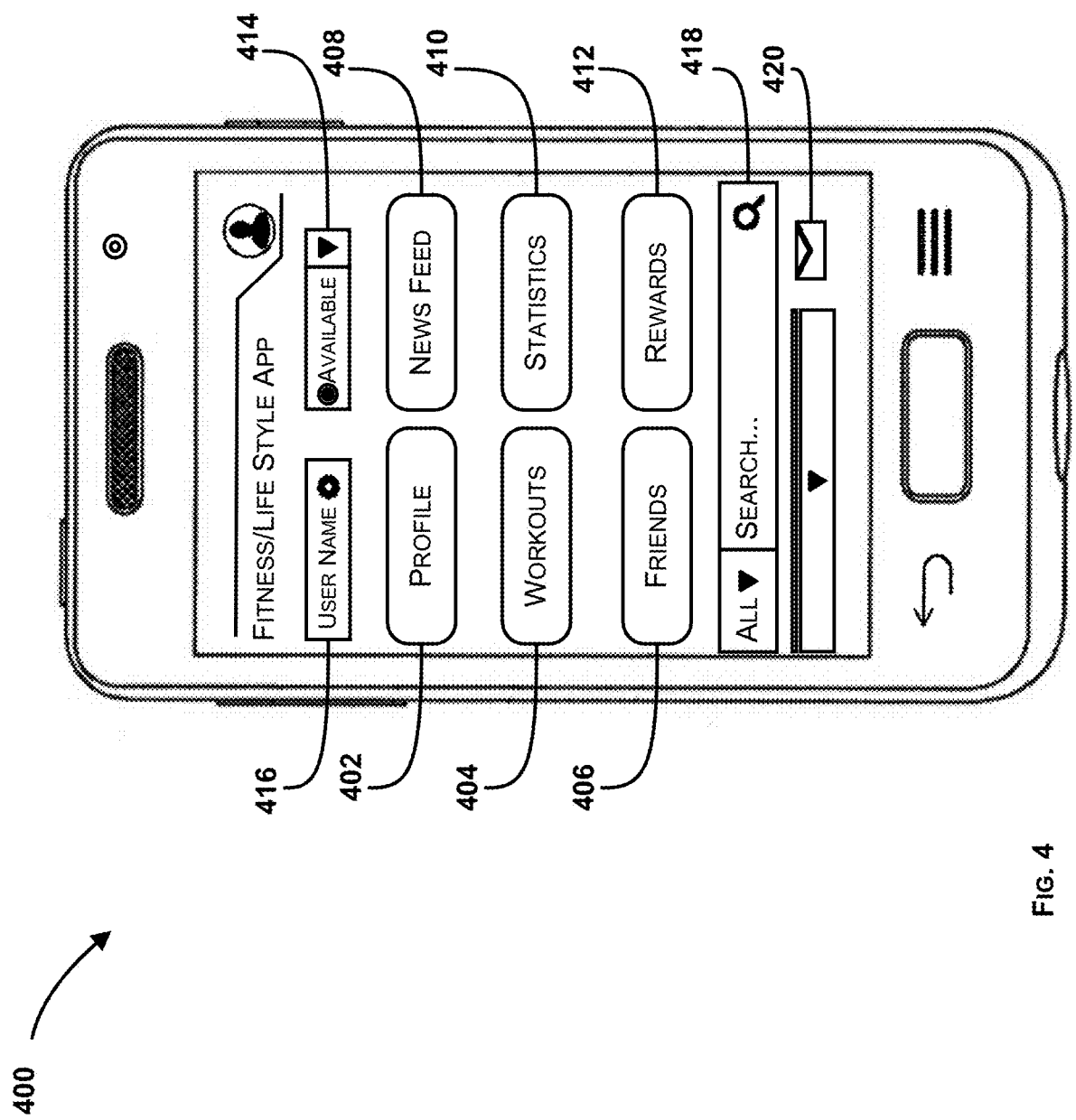
FIG. 4 is an exemplary illustration of a user interface of a mobile application for managing the fitness/lifestyle, according to an embodiment.

FIG. 4 is an exemplary illustration of a user interface of mobile an application for monitoring fitness/lifestyle of users. In FIG. 4, mobile application 400 includes profile 402, workouts 404, friends 406, news feed 408, statistics 410, rewards 412, status 414, user name 416, search 418, and email 420. It should be understood that mobile application 400 can include less fields, more fields, or different fields depending on the desired analysis goals.

In FIG. 4, mobile application 400 is implemented as software that can be downloaded and installed on client computing devices, carried by users, for interacting with a server system. Examples of mobile application 400 are GUI applications (Fitness/LifeStyle App) that may be available at, downloaded, and installed from a public software app stores or digital application distribution platforms, such as Apple iTunes®, Google Play® Store and Amazon.com®, among others. In these embodiments, mobile application 400 includes the following exemplary functions: allowing the user to create and manage a user account in the system profile 402; allowing the user to see the available workouts 404; allowing the user to invite and look at friends list 406; allowing the user to look at friends activity news feed 408; allowing the user to look at workout history of the user and/or friends statistics 410; allowing the user to check rewards for achieving goals 412; allowing the user to perform searches of people to send friend requests to 418; allowing the user to see the user name of the person connected to the system 416; allowing the user to receive emails from system 420; and allowing the user to see connection status 414.

Method for Tracking, Motivating, and Re-Undewriting a Group of Users

In some embodiments, a plurality of processes that are part of the electronic document issuance process are performed by one or more computing devices, such as computing device 200. The methods are implemented with components of the exemplary operating environments of FIGS. 1-4. The steps of this exemplary method are embodied in a computer readable medium containing computer readable code such that the steps are implemented when the computer readable code is executed by a computing device. While the blocks in the disclosed processes are shown in a particular order, the actual order may differ. In some embodiments, some steps may be performed in parallel.

Figure 5:
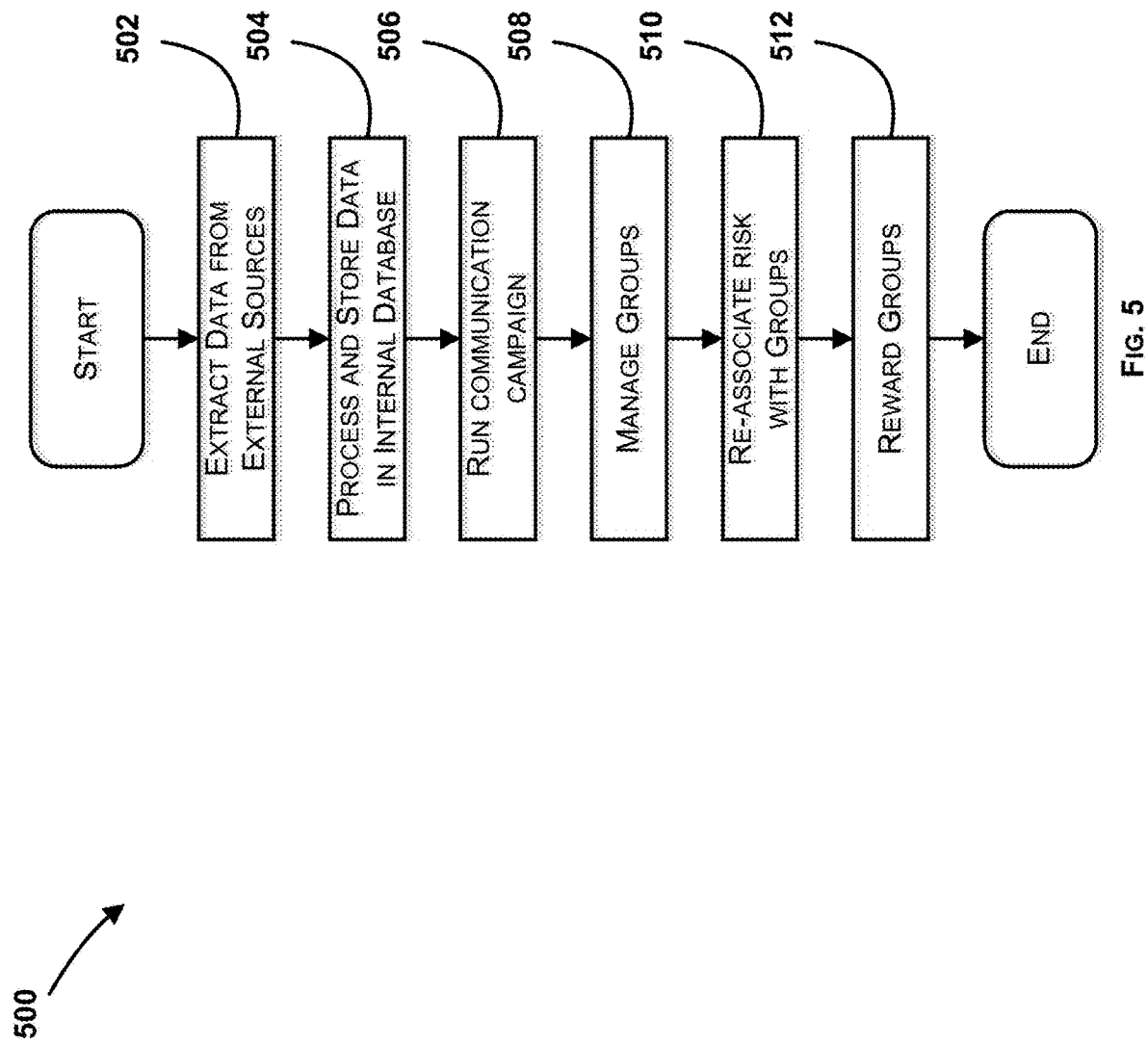
FIG. 5 is a flowchart of a method for tracking users to create or join groups with similar lifestyles attributes, according to an embodiment.

FIG. 5 illustrates a flowchart of a method for sending electronic documents with formatted paragraphs to a group of users that form groups that use wearables so as to monitor their fitness and lifestyle and report biometric information back to the server. In some embodiments, method 500 operates within an analytical engine configured to produce lists of address leads of users that share similar lifestyles and offer them the opportunity to join groups that report biometric data back to the server. In one embodiment, users within a group may be able to share information associated with biometric data collected by a wearable device.

In one or more embodiments, method 500 begins when the analytical engine, through the aid of the data extraction module, receives potential address leads of users (step 502). In these embodiments, the data extraction module within the analytical engine is configured to fetch and index, from social networks, users showing similar lifestyles that may be potential leads. Examples of potential leads include users that may exhibit a healthy lifestyle such as, for example, users that workout, eat healthy, jog/run every day, do sports, and the like. In one embodiment, the analytical engine may be configured to access morbidity rates, as understood in the art, of users stored in the server and enable the users to create groups with other users having similar morbidity rates, where morbidity rates are typically expressed in deaths per thousand (e.g., 9.5 deaths per thousand, or 0.95%). A similar morbidity rate may be considered one that is computed to be within a certain percentage of morbidity rates with other users or potential users. As an example, if a certain work commute has a morbidity rate of 0.08%, a similar morbidity rate may be considered other users with a work commute between 0.06% and 0.10%. Other ranges and examples of morbidity rates may be utilized, as well. The morbidity rates of each user may be determined and stored in an account of the users. Method 500 then advances to step 504.

The analytical engine can identify attributes of each user from a social networking site. Each attribute may be an occurrence of a word (e.g., running or biking), an association with a group (e.g., a running group), or an explicit reference to an event (e.g., "I just ran a marathon"). The analytical engine can determine that two or more users have a similar lifestyle based upon the identified attributes. For example, if two users each have a social networking site that mentions the word "run" more than 10 times in the last year, then these users may be considered to have a similar lifestyle. In another example, if one user recently posted about running a marathon, then that user may be considered to have a similar lifestyle to another user that is associated with a running group.

At step 504, the analytical engine, through the aid of the data processing module, processes and stores leads in an internal database to be used in further operations. In these embodiments, the data processing module within the analytical engine is configured to rank potential leads based on their lifestyle and produce leads that are stored within the internal database to be included in future electronic messaging campaigns. Method 500 then advances to step 506.

At step 506, the analytical engine, through the aid of the API, generates an electronic messaging campaign for the address leads previously selected in step 504. In these embodiments, the electronic messaging campaign offers the address leads previously selected and having similar lifestyles the opportunity to create or to join groups that can then be monitored using wearables having biometric sensors. Further to these embodiments, the an electronic messaging campaign includes personalized multimedia content files/data in social networks, where the personalized multimedia files/data may be automatically generated based on a variety of demographic and biometric factors of group or non-group members (e.g., friends of group members). The personalized multimedia files/data may be generated on a real-time (e.g., real-time request for a multimedia space in a social network or other user interface) or non-real-time (e.g., email multimedia files/data) basis for the users who use the social networks. Method 500 then advances to step 508.

At step 508, the analytical engine, through the aid of the API, manages the group of users that signs up for the electronic messaging campaign previously described in step 506. In these embodiments, the analytical engine, through the aid of the API, performs one or more of the following functions: sends out friend suggestions, creates groups, sends out wearables to registered users, receives biometric data from registered users, and the like. Method 500 then advances to step 510. In response to a group being created or a user joining a group, accounts of the users who are in the group are associated with the group using a data field or other parameter in a database or other data structure.

At step 510, the analytical engine runs different algorithms to process biometric data of groups of users and produces statistics that can later be used by a user to issue an electronic document comprising formatted paragraphs to groups of users by reporting the received biometric data to the server. The algorithms may parse and classify the biometric data information according to previously defined parameters to determine the overall behavior of the group. In one embodiment, big data processing techniques, as understood in the art, may be utilized to parse and classify the biometric data information. Method 500 then advances to step 512.

At step 512, the analytical engine suggests or recommends reward messages for group of users that show healthy lifestyles during a standard period of time. That is, the analytical engine may be configured to determine achievements of a collective group, such as walking more than a threshold total or average number of miles within a period of time (e.g., day, week, month), and determine a reward message for the group. The analytical engine 512, in recommending reward messages, may utilize rules that may be static (e.g., static threshold values) or dynamic (e.g., progressively increasing threshold values, relative threshold values with respect to one or more users within a group, values relative to other groups, etc.).

Figure 6:
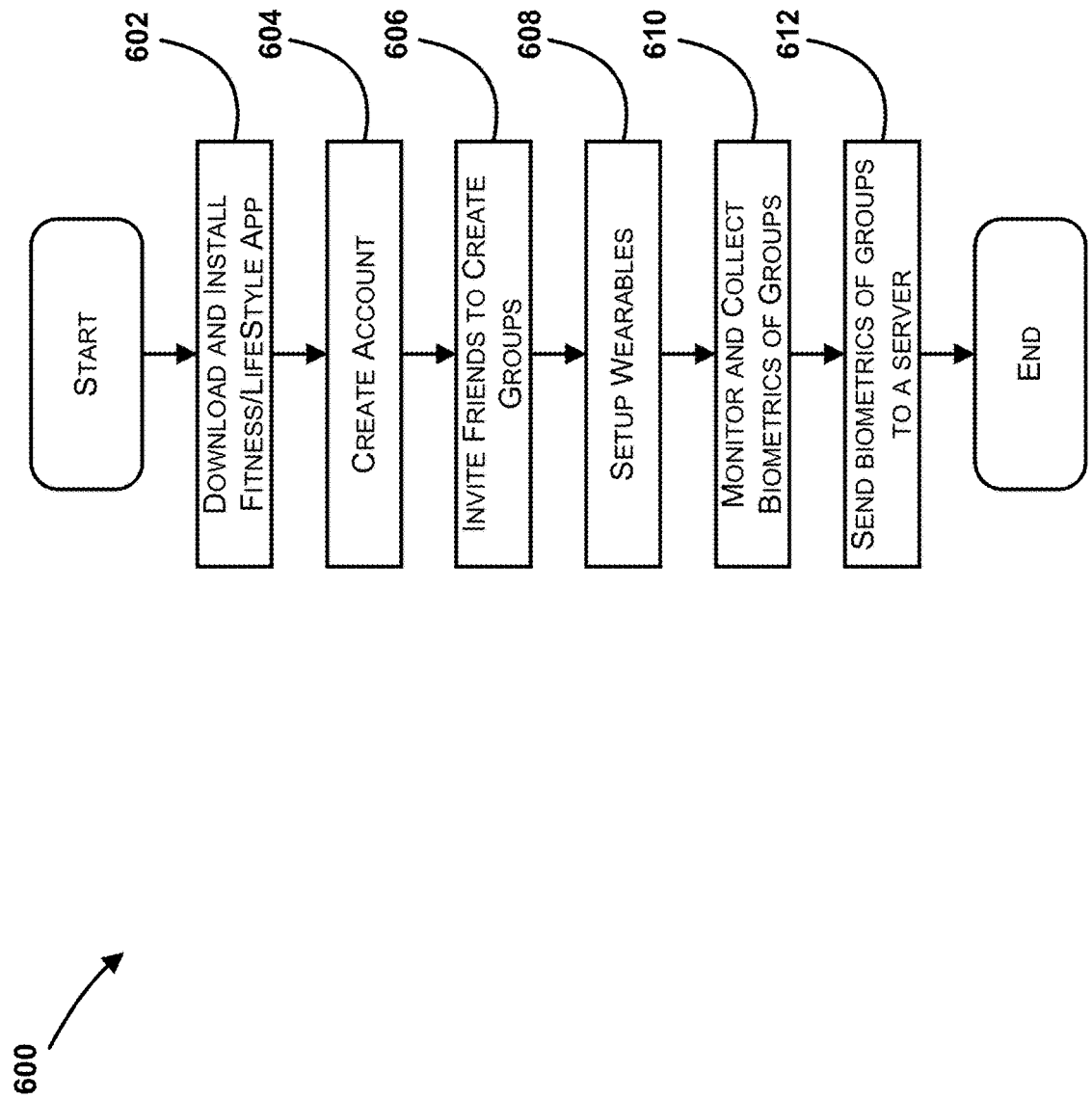
FIG. 6 is a flowchart of a method for operating a mobile application used for managing and monitoring the fitness/lifestyle of one or more users, according to an embodiment.

At step 506, the data gathering module determines if the data collected from the internal database and external sources matches an existing profile of a high risk individual stored in a high risk identification database. If the data collected matches the profile of a high risk individual, then method 500 advances to step 508. If the data collected does not match the profile of a high risk individual, then method 500 advances to step 510. Matching may include having data be exactly the same, within a range, outside a range, above a level, or below a level that is indicative of a high risk individual, FIG. 6 is a flowchart describing a method for operating a mobile application used for monitoring fitness/lifestyle of one or more users within the system. In some embodiments, method 600 operates within an API, resident in an analytical engine.

In one or more embodiments, method 600 begins when a user downloads and installs Fitness/LifeStyle app on a client computing devices for interacting with the system (step 602). In these embodiments, the Fitness/LifeStyle app, such as mobile application 400 of FIG. 4, are GUI applications that may be available at, downloaded, and installed from a public software app store or digital application distribution platform, such as Apple iTunes®, Google Play® Store and Amazon.com®, among others. Method 600 then advances to step 604.

At step 604, the user interface of the Fitness/LifeStyle app allows a user to create an account within the system of the server. In these embodiments, the API running on the analytical engine receives an account request including all personal data of the user who wishes to open an account. The API processes the information and creates an account within the system. Examples of personal data include name, emails, phone numbers, lifestyle preferences, workout preferences, demographics, geographics, occupations, and the like. Method 600 then advances to step 606.

At step 606, the user interface of the Fitness/Lifestyle app allows the user to invite friends having similar lifestyles to create or join groups. In these embodiments, the API running in the analytical engine sends and receives friend requests to/from users that wish to form groups with similar lifestyles. In one embodiment, the analytical engine may be configured to predetermine whether friends actually have similar lifestyles. The determination as to whether the friends have similar lifestyles may be initially based on user profiles of the friends that may include lifestyle related information so that the analytical engine can filter the friends prior to or after the user selects his or her friends. In the case of filtering prior to selection, the analytical engine may simply not include friends without similar lifestyles in a selectable list for other users (or friends) to invite the users with similar lifestyles to join a group. In the case of filtering after the selection, the analytical engine may notify the user that the friend does not meet the criteria of having a similar lifestyle. The notification may optionally provide reason(s) as to why the friend does not include a similar lifestyle. In another embodiment, the analytical engine may generate and send a notice to the friend that indicates that his or her friend invited him or her to be in a group, but that certain lifestyle parameters are deficient and, if corrected, would allow the friend to join the group. The analytical engine may, in addition to being used in creating or joining friends with similar lifestyles into groups, operate to track the members of the group and, in the event that one of the members fails to meet the similar lifestyle, notify the member that he or she is falling outside the lifestyle parameter(s) of the group. Method 600 then advances to step 608.

At step 608, the analytical engine pulls from the internal database the list of users that have joined the biometric monitoring program and generates orders to send out and deliver wearables to the users. In these embodiments, the registered users receive the wearables and pair them with the client computing devices. Examples of wearables include smartwatches, trackers, pedometers, activity trackers, and the like. Method 600 then advances to step 610.

At step 610, the Fitness/Lifestyle app receives from wearables the biometric data read from the users. In these embodiments, the biometric data collected from the users, but is not limited to, number of steps per day, workouts, heartbeat rates, levels of sweat, O2 saturation, and the like. Method 600 then advances to step 612.

At step 612, the Fitness/Life app sends via the communication network the biometric data collected from users for further analysis. In these embodiments, the API running on the analytical engine receives the biometric data and aggregates the information into groups to be used for issuing an electronic document at a later time by users of the system. For example. The electronic document may comprise formatted paragraphs. Method 600 ends.

One computer-implemented embodiment may include a method that extracts user data associated with users from an external source, the user data including information indicative of lifestyles of the respective users. The user data may be processed to populate a database, and the user data may be stored in the database. The user data stored in the database may be queried for users having attributes indicative of similar lifestyles. A social network user identifier of each user of the set of users having attributes indicative of similar lifestyles may be obtained. An electronic messaging content may be communicated to the social network user identifier of each user in the set of users having attributes indicative of similar lifestyles. A change in risk level for the set of users having attributes indicative of similar lifestyles may be calculated.

Extraction of the user data may include extracting user data from a social network. The user data may include at least one attribute indicative of a lifestyle of a user. Collection of the biometric data of a biometric parameter may be performed by a remote server. The biometric parameter may be monitored by a wearable device being worn by the respective users in a group of users having attributes indicative of similar lifestyles. The biometric data monitored by the wearable device may be processed to determine statistics of the biometric data of the users in the group. The statistics may include averages, maximums, standard deviations, and/or other statistics that may be used for group document issuance purposes. The users may be issued reward messages based on achievement datums as determined from the statistics of the collected biometric data. In determining rewards, the analytical engine may use rules and/or thresholds that enable the analytical engine to determine and recommend reward(s).

In addition, the biometric data monitored by the wearable device of each of the users of the group may be processed, and a determination as to whether the respective users qualify for receiving a reward message. The biometric data may be collected by the wearable devices used by the users of the group may be the same biometric parameter (e.g., steps taken during a day by each of the users in the group). The biometric data from the users may be collected via a wireless communications network with which a mobile electronic communications device of the respective users utilize, and stored in data records associated with the respective users in a database. The collected biometric data of the users of the group may be processed, and, based on the processed biometric data, suggest reward messages for the group of users during a period of time.

One aspect may include a user in a group being enabled to invite a user to join the group of users having attributes indicative of similar lifestyles. The process may enable an electronic messaging campaign may be conducted by communicating personalized multimedia content in one or more social networks based on lifestyles identified to be in association with users of the one or more social networks.

One embodiment of a method may include creating accounts for users who are associated with a biometric monitoring program. Users may be enabled to create groups of users associated with the biometric monitoring program, and having similar lifestyles using a downloadable application installed on a computing device of a user. Biometric data being monitored by a wearable device being used by respective users in a group of users having similar lifestyles may be collected. The biometric data collected by respective wearable devices of the users in the group may be processed to determine whether the group qualifies for receiving a reward message. A listing of the users in the group and associated biometric data from the users in the group may be transmitted.

In managing the users, a user may be enabled to search for friends with similar lifestyles via the downloadable application. Responsive to the user searching for other users with similar lifestyles, indicia (e.g., name photograph) of the friends with similar lifestyles may be caused to be selectably displayed for the user to invite to a group with similar lifestyles. The biometric data collected from each of the users in a group may be processed, and a determination of a collective achievement of the users in the group may be determined. In one embodiment, a reward message for the users in the group may be recommended in an automated manner based on the collective achievement of the group as determined from analyzing the biometric data of the users in the group.

Statistics from the biometric data of each user in the group may be generated, and each of the users in the group may be enabled to view at least a portion of the statistics. The group may be established by associating the accounts of the users in the group, and each of the users in the group may be enabled to share information associated with biometric data collected by the wearable devices being used by the users in the group. Statistical information derived from the biometric data may be enabled to be shared. For example, the statistical information may include a collective number of miles the group walked during a time period to motivate the users in the group, average heart rate during commute times, average heart rate during work hours, and so forth. It should be understood that the biometric data may include biometric data of one or more biometric parameter, such as heart rate, number of steps, movement, calories burned, or otherwise.

As a social network is created or expanded, users within the group may be enabled to search for friends with similar lifestyles who may or may not be within the group, thereby enabling the group to grow in a dynamic manner. A morbidity rate for the users may be computed, and the users may be enabled to create groups of users with similar lifestyles and morbidity rates. In one embodiment, the morbidity rates may not be presented to the users.

Figure 7:
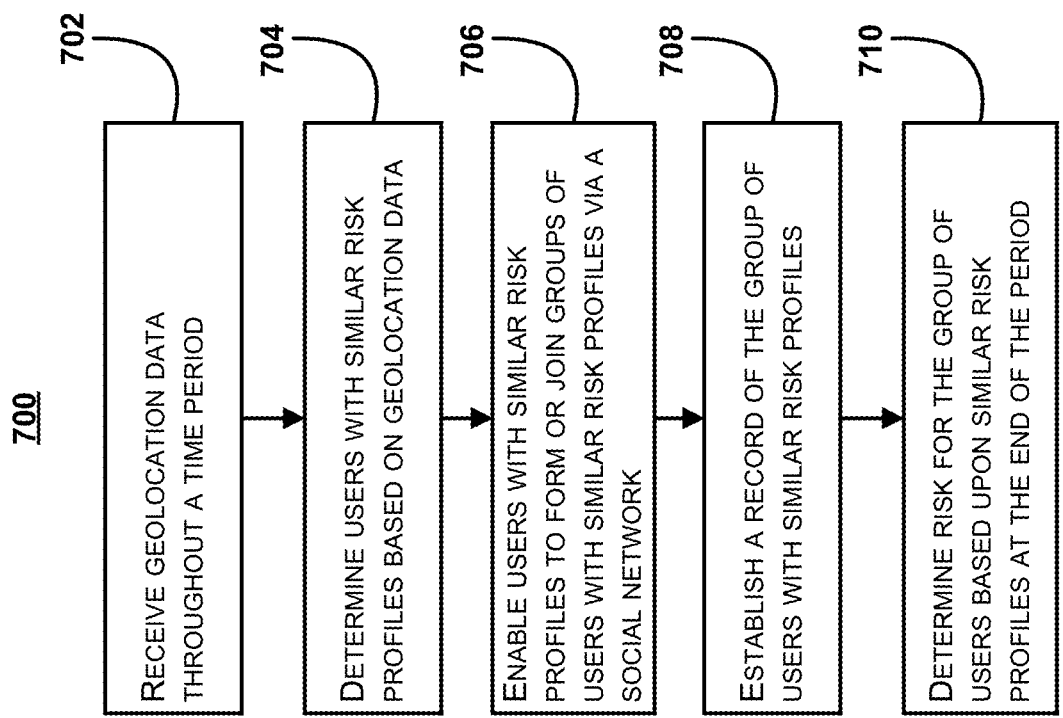
FIG. 7 is a flowchart of a process for providing an electronic document comprising formatted paragraphs to groups of user clients.

With regard to FIG. 7, a flowchart of a process 700 for use with groups of users is provided. The process 700 may start at step 702, geolocation data of the respective users throughout a time period may be received. The time period may extend for days, weeks, or months to enable the a user to get a day-to-day understanding of the users lifestyle, risk profile, or other factor that may enable the user to better assess the users. A risk profile may be a value determined by assessing lifestyle, geolocations traveled by a user, time of day the user travels in particular geolocations, and so on. In one embodiment, a map may be defined with risk values in specific geopolitical regions (e.g., zip codes), on specific roadways (e.g., highways versus side streets, intersections, etc.), specific modes of transportation (e.g., automobile, train, subway, bus, airplane), optionally as a function of particular times (e.g., rush hours, after dusk and before dawn, after midnight and before 6 AM), and so on. A downloadable mobile app for users to download to respective mobile devices may be provided and available via a communications network (e.g., at an online app store). In an embodiment, the downloadable mobile app may collect the geolocation data generated respective mobile devices of the users, or a network device, such as a server may track geolocation of the mobile devices of respective users. At step 704, a determination based on the geolocation data may be made of users with similar risk profiles. Similar risk profiles may be determined based on, at least in part, the geolocation data of the respective users throughout the time period. At step 706, users with similar risk profiles may be enabled to form or join groups of users with similar risk profiles via a social network. At step 708, a group of users with similar risk profiles may be established, and risk for the group of users based on the similar risk profiles may be calculated at the end of the time period at step 710.

In determining users with similar risk profiles based on geolocation data, the determination may include determining that the users travel within a predetermined distance threshold to and from work, for example. The distance range may also be correlated to a morbidity rate below a threshold level. For example, the predetermined distance threshold may include a distance of 5 miles, 10 miles, 15 miles, 20 miles, and so forth, where the distance may correlate to a risk factor score. Additionally, specific geolocation information, such as type of roadways, particular roadways, particular intersections, particular commute times, modes of transportations, and so forth may be used in determining morbidity rate and/or risk factor. A risk factor score may be a value that is determined based on one or more risk factors (e.g., total, average, or other statistical value produced by the risk factors). Moreover, the determination may include determining average speed, number of stops, and so on, that may contribute to the risk factor score and/or morbidity rate. Still yet, the specific geolocation data may be associated with crime, historical accident rates, historical traffic death rates, or any other historic information at geolocations of users that may play a part is affecting morbidity rate and/or risk factor score.

In one embodiment, a determination of users with similar travel types may be made. The travel types may be determined based on the geolocation data, and the similar travel types may include public transportation (e.g., trains, buses, ferries, airplanes) or personal transportation (e.g., automobile, motor cycle). In determining similar risk profiles, risk profiles of users who travel on similar types of transportation for similar amounts of time may be determined. Similar amounts of time may be durations of time that are, for example, within 5, 10, 20, or 30 minutes of one another, and may be varied based on type of roadways or mode of transportation taken by the users being compared and/or grouped. Still yet, a determination based on the geolocation data of the types of roadways on which the users drive may be made, and a determination of users with similar risk profiles who drive on similar types of roadways for similar amounts of time may be made.

In another embodiment, a biometric sensor to collect biometric data may be provided to users. Biometric data may be collected from the biometric sensor being used by the users, and the biometric data may be correlated with the geolocation data. A determination of a biometric response of the respective users in association with the geolocation data may be made. The biometric response, such as change in heart rate, may enable a determination as to how a user reacts to certain situations, such as rush hour traffic, work activities, stressful situations, non-stress situations, and so forth, which may be used to determine risk factors and profiles. A determination of users with similar biometric responses to similar geolocation data may be made, and users with similar biometric responses may be grouped.

Figure 8:
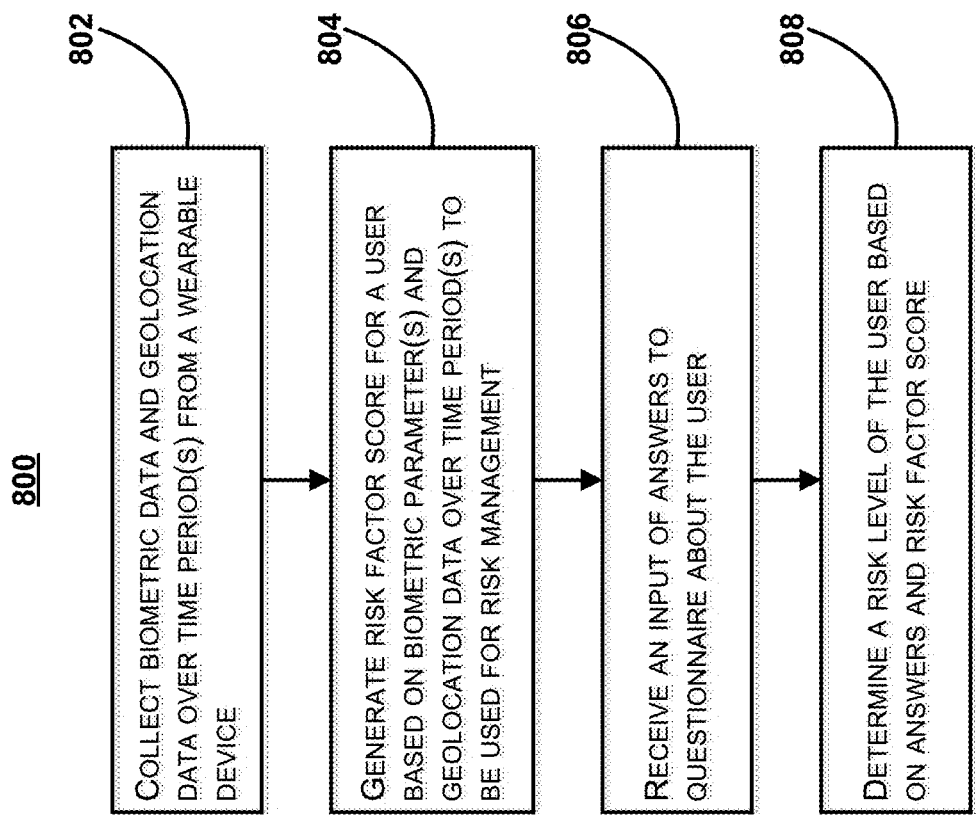
FIG. 8 is a flowchart of a process of providing an electronic document comprising formatted paragraphs to a user using non-invasive techniques.

With regard to FIG. 8, a flowchart of a process 800 of a user using non-invasive techniques is shown. Invasive techniques may include blood samples, but for the purposes of this description, may include urine samples, stool samples, or other samples of bodily fluids or tissue that are used for determining health and risk factors of a user. In other words, the non-invasive techniques are independent of collecting paramed data. The process 800 may start at step 802 by collecting biometric data of the at least one biometric parameter and geolocation data over at least one time period from a wearable device. The wearable device may be configured to collect at least one biometric parameter from a user. The biometric parameters may include number of steps, heart rate, blood sugar level, energy usage, movement, or any other dynamic biometric measurement or combination thereof, as understood in the art. The time period(s) may include work commuting times, sleep times, mornings, afternoons, work periods, workout times, and so forth. At step 806, a risk factor score for the user based on the biometric parameter(s) and geolocation data over the time period(s) may be generated. The risk factor score may be based on the combined biometric data of the biometric parameter(s) and geolocation data.

At step 808, an input of answers to a questionnaire about the user may be received. The questionnaire may be conventional or may include additional information, such as typical drive times, work geolocation, or any other information that can be used in correlating biometric parameter (s) and geolocation data to produce a risk factor score. At step 810, a risk level of the user based on the answers and risk factor score may be calculated.

In one embodiment, the time period(s) may include commute times, and biometric parameter(s) include heart rate. The time period(s) may additionally or alternatively include work times, and the biometric parameter(s) may include heart rate. A determination may be made of an activity (e.g., sleep, work, exercise) of the user during time period(s). One aspect may include providing a mobile app to be downloaded to a mobile device of the user, where the mobile device may be selectively in wireless communication with the wearable device. The mobile app may be configured to collect the biometric data being captured by the wearable device. A group of users having similar risk factor scores may be generated. In being enabled to participate, the users may be provided with an interface (e.g., graphical user interface, such as a website or app user interface) via which the users may register to join the group.

The risk factor scores of the each of the users in the group may be generated by processing additional biometric data and geolocation data. Responsive to the risk factor scores in the group improving in the aggregate, a reward message to which the users in the group are set to receive may be recommended. In one embodiment, the recommendation may be automatically made based on rules that relate to a correlation of biometric data and geolocation data. Moreover, the biometric data of the biometric parameter(s) and geolocation data over the at least one time period may be correlated. By correlating the biometric and geolocation data, a determination as to how a user reacts to stresses in various situations may be made. A determination of similar lifestyles and medical history based on the answers and the geolocation data may be made. A determination of lifestyle of the user based on the geolocation data and biometric data may also be made. That is, lifestyle may be determined based on the geolocations. The lifestyle may include type of activities, amount of commute time, work stress, amount of leisure time (e.g., golfing, fishing, etc.), specific retail establishments visited, specific entertainment establishments visited, and so on. In one embodiment, a risk factor score may be influenced by mobile device operation during driving times (e.g., texting or talking while driving), and a mobile app may track mobile device usage and geolocations for determining usage while commuting. Similar medical histories may be determined based on general and/or specific medical conditions of the users. For example, general medical histories may include particular diseases, such as heart disease, while specific medical histories may be particular stage of disease, family history of disease, or general condition of health.

The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

When implemented in hardware, the functionality may be implemented within circuitry of a wireless signal processing circuit that may be suitable for use in a wireless receiver or mobile device. Such a wireless signal processing circuit may include circuits for accomplishing the signal measuring and calculating steps described in the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

Any reference to claim elements in the singular, for example, using the articles "a," "an" or "the," is not to be construed as limiting the element to the singular.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method comprising:
receiving, by a first server, over a wide area network, a plurality of geolocation data sets at different time periods from a plurality of clients;
receiving, by the first server, over the wide area network, a plurality of biometric data sets from a plurality of wearable computers associated with the plurality of clients;
receiving, by the first server, over the wide area network, an input of lifestyle criteria based on an activity level of each client;
storing, by the first server, the geolocation data sets, the biometric data sets, and the lifestyle criteria in a plurality of database records, each database record associated with one of the plurality of clients;
extracting, by the first server, a plurality of travel attributes from the geolocation data sets within the different time periods in the database records;
determining, by the first server, a risk profile based on the travel attributes of each geolocation data set and a corresponding time period;
determining, by the first server, a correlation between each geolocation data set and each biometric data set within the different time periods based on a time value of each geolocation data set and a time value of each biometric data set, wherein the correlation indicates each client's biometric response corresponding to the risk profile of each respective geolocation and time period;

determining, by the first server, a risk factor score for each client based on the correlation between each geolocation data set and each biometric data set within the different time periods;

determining, by the first server, a lifestyle for each client based on the geolocation data set and input lifestyle criteria, wherein each lifestyle determination is a measurement of fitness practiced by each client;

identifying, by the first server, a set of records corresponding to a set of clients that share a risk factor score within a predetermined range and a same lifestyle determination;

grouping, by the first server, the set of the records corresponding to the set of clients that share the risk factor score within the predetermined range and the same lifestyle determination;

accessing, by the first server, over the wide area network, a social network service hosted on a second server;

generating, by the first server, a group on the social network service comprising the set of clients that share the risk factor score within the predetermined range and the same lifestyle determination;

transmitting, by the second server using an application programming interface, an electronic message to the set of clients within the group, the electronic message configured to invite the set of clients to join the group on the social network service;

assigning, by the first server, the set of records to the group such that a risk statistic of the group can be determined based on a plurality of communications between the clients in the group; and in response to determining, by the first server, that the risk statistic exceeds a predetermined threshold, transmitting, by the second server, a message informative of the risk statistic exceeding the threshold to an electronic messaging address associated with each client within the group.

2. The method of claim 1, wherein at least one of the travel attributes is based on a movement of at least one of the clients along a distance between a pair of geolocations during a time period, wherein the pair of geolocations are predetermined before the receiving and stored in at least one of the database records, wherein the time period is predetermined before the receiving and stored in the at least one of the database records.

3. The method of claim 2, further comprising:

determining, by the server, a morbidity rate and a threshold for the at least one of the clients based on at least one of the records associated with the at least one of the clients;

determining, by the server, before the extracting, the distance based on the morbidity rate being below the threshold.

4. The method of claim 1, further comprising:

determining, by the server, a morbidity rate for a route;

determining, by the server, a threshold for at least one of the clients based on at least one of the records associated with the at least one of the clients, wherein at least one of the travel attributes is based on a movement of the at least one of the clients along the route associated with the morbidity rate being below the threshold.

5. The method of claim 1, wherein at least two of the geolocation data sets correspond to a single time period and to at least two train routes, wherein the set of the records comprises the at least two of the geolocation data sets.

6. The method of claim 1, wherein at least two of the geolocation data sets correspond to a single time period and to at least two roadways, wherein the set of the records comprises the at least two of the geolocation data sets.

7. The method of claim 1, further comprising:

extracting, by the server, a plurality of characteristics from the biometric data sets in the database records;

determining, by the server, at least two of the database records that share the characteristics, wherein the set of records comprises the at least two of the database records.

* * * * *